United States Patent [19]

Adair

[11] Patent Number: 5,630,782

[45] Date of Patent: *May 20, 1997

[54] STERILIZABLE ENDOSCOPE WITH SEPARABLE AUXILIARY ASSEMBLY

[76] Inventor: Edwin L. Adair, 317 Paragon Way, Castle Pines Village, Colo. 80104

[*] Notice: The term of this patent shall not extend beyond the expiration date of Pat. No. 5,489,256.

[21] Appl. No.: 399,821

[22] Filed: Mar. 7, 1995

Related U.S. Application Data

[63] Continuation-in-part of Ser. No. 333,360, Nov. 2, 1994, Pat. No. 5,489,256, which is a continuation of Ser. No. 938,629, Sep. 1, 1992, abandoned.

[51] Int. Cl.$^6$ ....................................................... A61B 1/00
[52] U.S. Cl. ........................... 600/133; 600/123; 600/153; 600/156; 600/127
[58] Field of Search ...................................... 600/121, 123, 600/124, 125, 127, 133, 153, 156, 158, 203, 205, 186, 187, 175; 359/510

[56] References Cited

U.S. PATENT DOCUMENTS

| | | | |
|---|---|---|---|
| 3,043,309 | 7/1962 | McCarthy | 128/898 |
| 4,737,142 | 4/1988 | Hekele | 128/6 X |
| 4,869,238 | 9/1989 | Opie et al. | 128/6 |
| 4,878,485 | 11/1989 | Adair | 128/6 |
| 4,984,563 | 1/1991 | Renaud | 128/6 |
| 5,125,143 | 6/1992 | Takahashi | 128/4 X |
| 5,154,164 | 10/1992 | Chikama | 128/4 |
| 5,167,220 | 12/1992 | Brown | 128/4 |
| 5,188,094 | 2/1993 | Adair | 128/6 |
| 5,188,596 | 2/1993 | Condon et al. | 128/6 X |
| 5,251,613 | 10/1993 | Adair | 128/6 |

*Primary Examiner*—Beverly M. Flanagan
*Attorney, Agent, or Firm*—Fields & Johnson, P.C.

[57] ABSTRACT

An endoscope with separable auxiliary assembly is provided that includes a cylindrical shaped endoscope that is insertable within a sterile end cap with attached sterile drape, the drape being extendable over the length of the endoscope and its trailing cables thus isolating the endoscope and its trailing cables from the environment. A sterile separable channel section is provided that releasably attaches to the end cap. The separable channel section has a plurality of longitudinal channels running therethrough so that operative fluids, gases or operative instruments may be applied to the surgical site. To enable a surgeon to obtain selectable images of an operative site, a detachable viewing head may be attached to the distal end of the endoscope prior to placement of the endoscope inside the end cap.

48 Claims, 6 Drawing Sheets

STERILIZABLE ENDOSCOPE WITH SEPARABLE AUXILIARY ASSEMBLY

This application is a continuation-in-part application of my U.S. Ser. No. 08/333,360, filed Nov. 2, 1994 and entitled "Sterilizable Endoscope With Separable Disposable Tube Assembly", now U.S. Pat. No. 5,489,256, which is a continuation of my U.S. Ser. No. 07/938,629 filed Sep. 1, 1992 and entitled "Sterilizable Endoscope With Separable Tube Assembly", now abandoned.

TECHNICAL FIELD

This invention relates to an endoscope that is shielded by a sterile end cap with an attached sterile drape wherein a sterile separable channel section removably attaches to the end cap. The end cap, drape and channel section are disposable after use and the same endoscope may be used for subsequent operative procedures without resterilization.

BACKGROUND ART

In recent years the popularity of endoscopic surgery has proliferated. This has occurred because of the advances in technology which allow smaller and smaller endoscopes to be used, thereby permitting operative procedures to be undertaken in a less invasive manner than was previously possible. Thus, the patient suffers less trauma, recuperates much more rapidly and experiences less pain and discomfort than with more conventional surgical procedures.

Because of the sophisticated optics and electro-optics contained in modern endoscopes, they generally are very expensive. In order for this expense to be justified, they must be reused with a large number of patients.

Of course, reuse requires that the endoscope must be sterilized or at least disinfected after use with each patient prior to use with the next patient. One protocol for sterilization involves immersing the endoscope in a disinfectant solution for a predetermined period of time. It is also important to flush the channels inside the endoscope which carry gases, fluids, or which receive operative instruments. When using the disinfectant, sometimes the endoscope is not placed in the disinfecting solution for a sufficient length of time nor are the channels flushed out completely because of the urgency to get the endoscope back into service as soon as possible. Over time, the disinfectant solution may lose some of its strength, thereby limiting its effectiveness. Another protocol is to heat sterilize the endoscope by placing it in an autoclave. However, the optics and electronics of many endoscopes will not permit them to be subjected to heat sterilization.

Because of these shortcomings, studies have shown that transmission of infectious diseases from one patient to another has occurred in many instances. By way of example, transmission of salmonella typhi has been reported. In addition, pseudomonas aeruginosa has been linked to endoscopy. Also, an outbreak of serratia marcescens has been associated with the use of a bronchoscope. Furthermore, Hepatitis B has been transmitted by endoscopes when the endoscopes were processed in an inappropriate manner between patients. Finally, with respect to endoscope use on patients with acquired immune deficiency syndrome (AIDS), it has been found that the sterilizing procedures have not always removed contamination of the human immunodeficiency virus (HIV). This list is not exhaustive by any means.

A high-level of disinfection failures among gastrointestinal endoscopes have been noted, as well as failures in bronchoscopes, laryngoscopes and other devices. This may be due to the fact that they are long and narrow and have internal channels that are difficult to sterilize.

Another shortcoming of the prior art is that when a tube assembly is attached to the distal end of an endoscope not having integrally formed internal passageways, the resulting cross-sectional shape was greatly increased because the tube assembly was not structurally designed to mate with the endoscope. A larger cross-sectional shape results in increased trauma to patients undergoing surgery.

From the foregoing, it is apparent that endoscopes are needed that can be more easily and effectively sterilized, and that maintain a small size to accommodate minimal invasive surgery.

DISCLOSURE OF THE INVENTION

In accordance with the present invention, an endoscope with a separable auxiliary assembly in one configuration is provided. The separable auxiliary assembly includes a sterile disposable separable channel section, and a sterile disposable end cap with an attached sterile drape. The endoscope is of the type that includes an elongated capsule, of the size of a medicinal capsule, and a substantially cylindrical housing with a transparent window at the distal end thereof for containing the endoscope optics. An image sensor such as a CCD is mounted adjacent the window within the capsule. An image transmitting cable or conduit with multiple conductors each has a distal end connected to the image sensor circuit board and a proximal end connected through a series of cables to a video control unit. From the video control unit, signals are transmitted to a video monitor which displays the image in black and white or color. A plurality of light transmitting fibers are disposed within the capsule, each having a distal end adjacent to the window within the capsule, the fibers extending proximally from the capsule for transmitting light to a site under investigation from a remote light source.

An end cap is provided that is configured to house the distal end of the capsule and shield it from the sterile operating environment. The proximal end of the end cap provides a means of attachment for the sterile drape that encloses the remaining portion of the capsule and the trailing endoscope cables.

The separable channel section is removably attached to the end cap in a fixed relationship and has at least one longitudinal channel extending internally therethrough for transmitting fluids, gas or for receiving an operative instrument. A flexible tube is connected to the proximal end of the channel for supplying fluid, gas or the operative instrument from a remote location. The separable channel section and end cap with attached drape are disposable after use on a patient. Thus, the endoscope is available for reuse with another separable auxiliary assembly on the next patient without having to resterilize or disinfect the endoscope.

In operation, the capsule portion of the endoscope is inserted within the end cap and the drape is extended over the capsule to completely shield the endoscope and its trailing cables from the sterile operating area. The separable channel section may then be attached to the end cap.

More particularly, the separable channel section is configured to attach to the end cap to minimize the cross-sectional size thereof. The separable channel section includes a longitudinal guide or key which may be snap fit or slidably engageable with a longitudinal guideway or keyway formed on the exterior surface of the end cap. Conveniently, the separable channel section is configured such that when the end cap and the separable section are attached, they form a circular, oblong or substantially oval cross-sectional shape.

Other means of attachment may be used to attach the separable channel section to the end cap. For example, a magnetic attachment or the use of an elastic band may be used. Those schooled in the art may envision other methods of holding the separable channel section in the releasable yet fixed relationship to the end cap.

The same inventive concept of using a separable channel section can be used with a steerable endoscope. The separable channel section may include a guide wire channel which receives a guide wire extending from the endoscope. Thus, if the separable channel section and end cap are constructed of a flexible material, the guide wire extending through the guide wire channel can be used to steer the distal end of the endoscope capsule housed within the end cap.

In operation, the endoscope capsule housed by the separable auxiliary assembly is inserted into a bodily passageway to the desired operative site. The site is investigated through the image produced by the endoscope and the necessary operative procedures are carried out through channels within the separable channel section. The endoscope and separable auxiliary assembly are then removed from the bodily passageway whereupon the endoscope capsule may then be separated from the auxiliary assembly. Since the endoscope is completely shielded from the operative site, the same endoscope may be used in a subsequent surgical procedure by simply utilizing a new separable auxiliary assembly. Thus, the need to sterilize the endoscope is eliminated which greatly improves surgical procedures both in terms of the cost and labor associated with sterilization of such endoscopic devices.

In order to enhance the viewing field of the operative sight, a detachable viewing head may be attached to the distal end of the endoscope prior to placing the end cap over the endoscope. Detachable viewing heads offer a wide variety of optical lens combinations which enable a surgeon to view the operative site at the desired angle or magnification.

With this described apparatus, a method has also been provided for utilizing a separable auxiliary assembly on a conventional endoscope. The method includes placing a sterile end cap with attached drape over a conventional endoscope and extending the drape over the exposed length of the endoscope and its trailing cables. The separable channel section is then releasably attached to the distal end of the end cap in a fixed position. The operative site is investigated and the necessary operative procedures are performed. After use, the endoscope is removed from inside the extended drape and end cap, and the separable channel section, end cap and drape may be thrown away. A detachable viewing head may be used in conjunction with the aforementioned method enabling precise and selectable viewing of the operative area.

BEST MODE FOR CARRYING OUT THE INVENTION

Figures 1, 2:
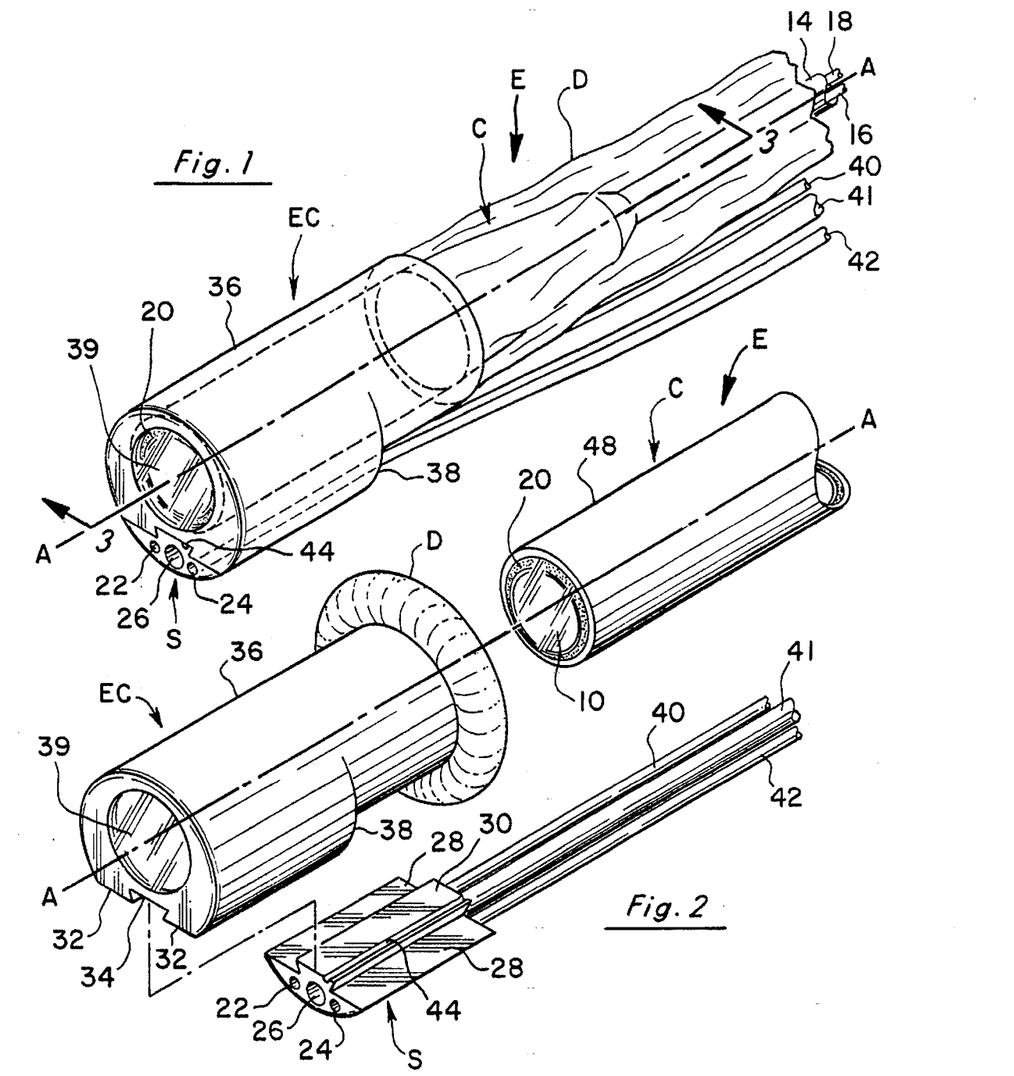
FIG. 1 is a fragmentary perspective view of the sterilizable endoscope with separable auxiliary assembly of this invention, with the drape extended.
FIG. 2 is a fragmentary exploded perspective view of the invention of FIG. 1, with the drape in a rolled position prior to use.
Figure 3:
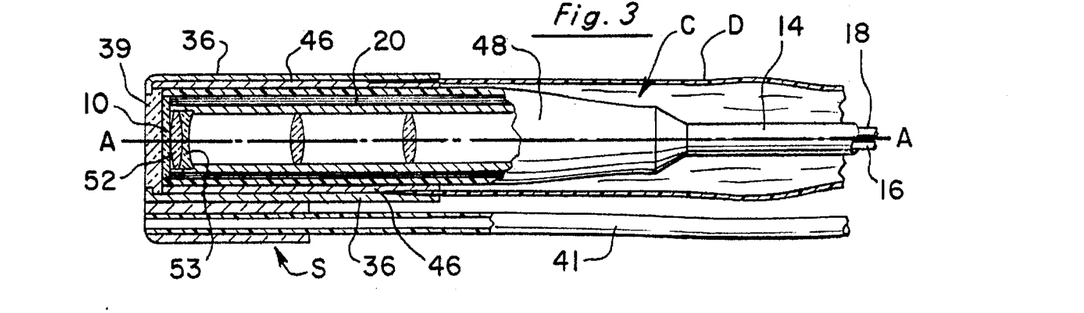
FIG. 3 is a partial longitudinal section taken along line 3—3 of FIG. 1 illustrating the interior relationship of the elements making up the invention when the invention is assembled for use.

In accordance with one embodiment of this invention, an endoscope E is provided, as best seen in FIGS. 1–3, which includes a capsule portion C that is inserted within a protective end cap EC. A rolled-up drape D is attached to a proximal end of the end cap EC. Releasably attached to the end cap EC is a disposable or throwaway separable channel section S. The end cap EC, drape D and separable channel section S comprise the separable auxiliary assembly of this invention. The end cap EC, attached drape D and separable channel section S are packaged prior to use as completely sterile items. As shown in FIG. 2, the endoscope E includes the distal portion or capsule C which has a window 10 for sealing the interior of the capsule C from the environment. Typically, one or more optical fibers 20 terminate within the capsule C at the window 10. Disposed within the interior of capsule C is an imaging chip such as a CCD (not shown) and associated electrical leads (not shown) which connect to transmission wires 18 within conduit 14. In operation, the optical fibers 20 provide light to the operative site and the imaging chip receives a visual image of the operating site which is then transmitted via the electrical leads through wires 18. As shown in FIG. 1, the proximal end of capsule C is connected to the conduit 14 which extends proximally away from the capsule C and which houses wires 18 and bundled optical fiber cable 16 that branches out within capsule C into the peripherally arranged fibers 20. Although one embodiment of an endoscope is illustrated herein, it will be understood that any endoscope with a generally cylindrical shape may be used in conjunction with the separable auxiliary assembly of this invention.

The separable channel section S may include a pair of fluid or gas channels 22 and 24 and an operative channel 26. In communication with channels 22, 24 and 26 are corresponding tubes 40–42, respectively, which allow fluids, gas or a surgical instrument to be passed therethrough so that the fluids, gas or operative instrument may be applied to the operative site. FIGS. 1 and 2 illustrate a pair of fluid or gas channels and a single operative channel, however, it will be understood by those skilled in the art that any number or combination of channels may be used with the separable channel section S in order to transmit the needed operative fluid, gas or surgical instruments to the operative site. Conveniently, the channel section S includes a pair of flats 28 which are located on opposing sides of a key 30. Accordingly, end cap EC includes a pair of corresponding flats 32 with a keyway 34 positioned therebetween. Thus, in order to attach the separable channel section S to the end cap EC, the channel section S is simply snapped into place, or alternatively, key 30 is slid along keyway 34 until the distal end of the separable channel section S is flush with the distal end of the endoscope EC. When the end cap EC and separable channel section S are joined, a substantially circular, oblong, or oval cross-sectional shape is achieved depending upon the particular end cap and separable channel section embodiment.

Although key 30 is shown as being formed on the separable channel section S, it is to be understood that key 30 could be formed on the end cap EC. Accordingly, keyway 34 would be formed on separable channel section S to complement the protruding key 30 located on the end cap EC.

Central axis A—A is shown extending longitudinally through the invention such that when the separable section S and end cap EC are attached, the resulting cross-sectional area can be defined from the axis. Specifically, axis A—A passes through the approximate geometric center of the resulting cross-sectional area.

As further illustrated in FIG. 2, the end cap EC includes an outer end cap wall 36 having a proximal end which attaches to the sterile drape D which may be rolled as shown prior to use. As best seen in FIG. 3, the end cap EC also includes an inner wall 46 wherein the outer wall 36 and inner wall 46 capture the distal end of the drape D, thus holding it in a fixed relationship thereto. The end cap EC also includes a window 39 attached to the distal end of the end cap EC which enables light emanating from optical fibers 20 to be conveyed to the operative site. In order to compensate for tubes 40–42 which are positioned exteriorly of capsule outer surface 48, the end cap EC is configured to include a protrusion 38 which conveniently allows the tubes 40–42 to extend proximally away from the end cap EC and to be kept in parallel relationship with the proximally extending conduit 14.

In the event that endoscope E is of the type that includes a steering mechanism, guide wire channel 44 is formed integrally with separable channel section S along one flat 28 enabling some articulation of the very distal tip of the capsule C. Additionally, one or more guide wire channels (not shown) may be formed on the inner wall 46 of end cap EC so that the distal end of the endoscope may be articulated in a more precise direction. The end cap EC and separable channel section S may be made of a flexible material to enhance omni-directional articulation of the distal end of the endoscope.

FIG. 3 illustrates the interior relationship of the elements of the invention when the endoscope is placed in use. As shown, the drape D is unrolled to extend over the capsule C and the trailing conduit 14. The endoscope E includes a plurality of optical fibers 20 which terminate at the window 10 as shown in FIG. 2. As is commonly known in the art, endoscope E may include one or more endoscope lenses, such as lenses 52 and 53, in order to provide the desired image to the CCD located within endoscope E.

Figures 4, 5, 6:
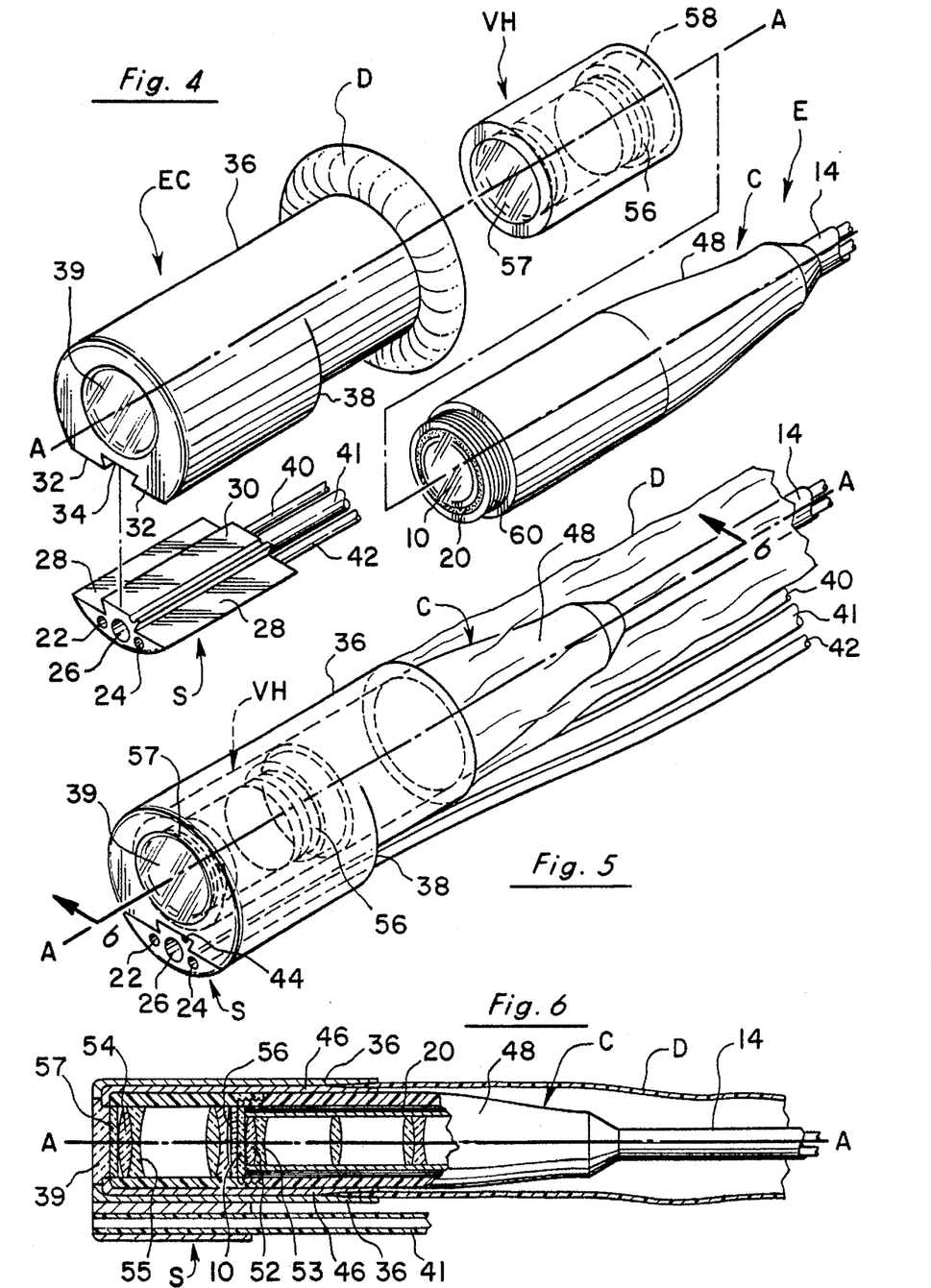
FIG. 4 is a fragmentary exploded perspective view of another embodiment of the invention that illustrates a detachable viewing head that is engageable with the distal end of the endoscope, with the drape rolled up.
FIG. 5 is a fragmentary perspective view of the invention of FIG. 4 with the drape extended and having phantom lines illustrating the relationship between the end cap, detachable viewing head and endoscope.
FIG. 6 is a partial longitudinal section taken along line 6—6 of FIG. 5 illustrating the interior relationship of the elements making up the invention when the invention is assembled for use.

As illustrated in FIGS. 4 and 5, this invention may include an alternative embodiment wherein a viewing head VH is attachable to the distal end of the endoscope E. A detachable viewing head VH of the type shown in FIG. 4 can be used to further enhance options to the surgeon in viewing the operative site. Each viewing head may contain its own set of lenses or optics, such as lenses 54 and 55 as shown in FIG. 6, in order that the desired type of image is transmitted to the CCD. The viewing head VH further includes a proximal window 56 and a distal window 57 enabling light to be transmitted from the light fibers 20 and through the viewing head VH to the operative site. According to one method, the viewing head VH may be attached to the endoscope E by simply utilizing internal threads 58 on the viewing head and corresponding external thread 60 on the endoscope E. It will be understood by those skilled in the art that a number of other ways may be used to attach the viewing head to the endoscope, such as by a ball detent, compression fitting or other appropriate means.

FIG. 6 illustrates the internal relationship of the elements of the embodiment of FIG. 4, wherein the viewing head VH includes the plurality of viewing head lenses 54 and 55 in order that a surgeon may obtain the desired image of an operative site.

Figure 7:
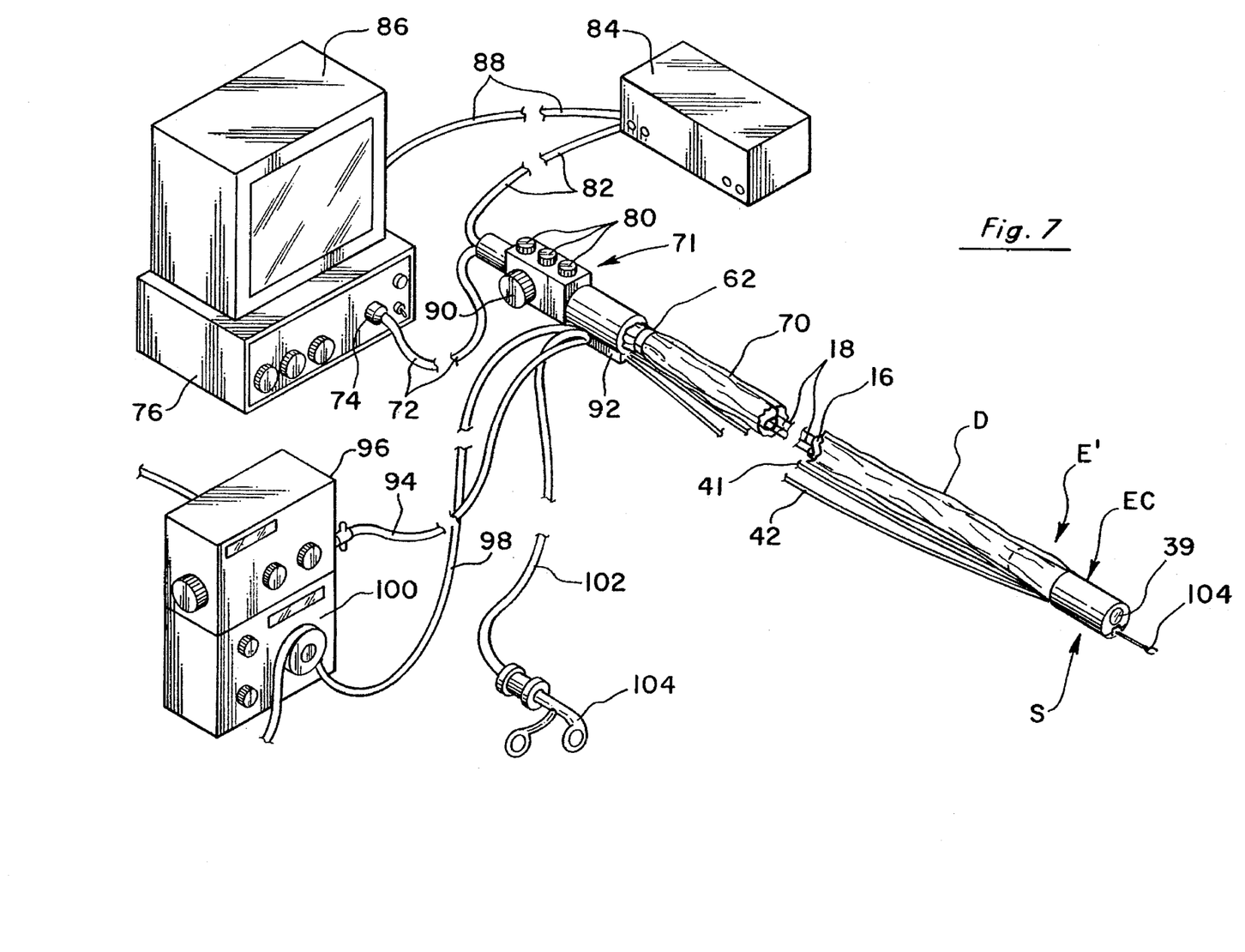
FIG. 7 is a perspective view of the invention of FIG. 1 connected through a control member to suitable gas supplying and instrument supplying channels, and connected to a video monitor.

FIG. 7 illustrates the invention of FIG. 1 as it is used with equipment that provides operative fluid, gas, instruments and a viewing monitor. This figure shows the endoscope and separable auxiliary assembly greatly enlarged in comparison to the equipment in order to illustrate structural detail of the endoscope and separable auxiliary assembly. Specifically, endoscope E' may be of the type having an elongated barrel 70. The proximal end of drape D may be attached to the barrel 70 by means of a retainer band 62. A miniaturized video camera 71 attaches to the endoscope E'. Running into one end of the camera 71 may be a light source cable 72 which in turn connects by fitting 74 to a source of light 76. Camera 71 may include a plurality of controls 80. An image conduit 82 extending from the camera 71 connects with a video control unit 84 which in turn connects to a video monitor 86 via cable 88. Thus, an image received on the CCD (not shown) is transmitted through electrical leads (not shown) to transmission wires 18, to the camera 80, through image conduit 82 to the video control unit 84, and then to the video monitor 86 via the cable 88. Camera 71 may also be of the type that includes a steering knob 90 which is connected to a plurality of steering wires (not shown) which extend through barrel 70 and communicate with guide wire channel 44 of the separable channel section S and guide wire channels (not shown) formed on the inner wall 46 of end cap EC. Tubes 40–42 parallel the barrel 70 and are attached to the camera 71 by means of a tube housing 92. As shown in FIG. 7, tubes 40–42 may communicate with sources such as vacuum, fluid, or instruments. Accordingly, vacuum hose 94 communicates with vacuum pump 96. Fluid hose 98 is attached to a fluid pump 100. Instrument tube 102 receives forceps 104 which travel through tube 102, tube 41 and channel 26.

Figures 8, 9:
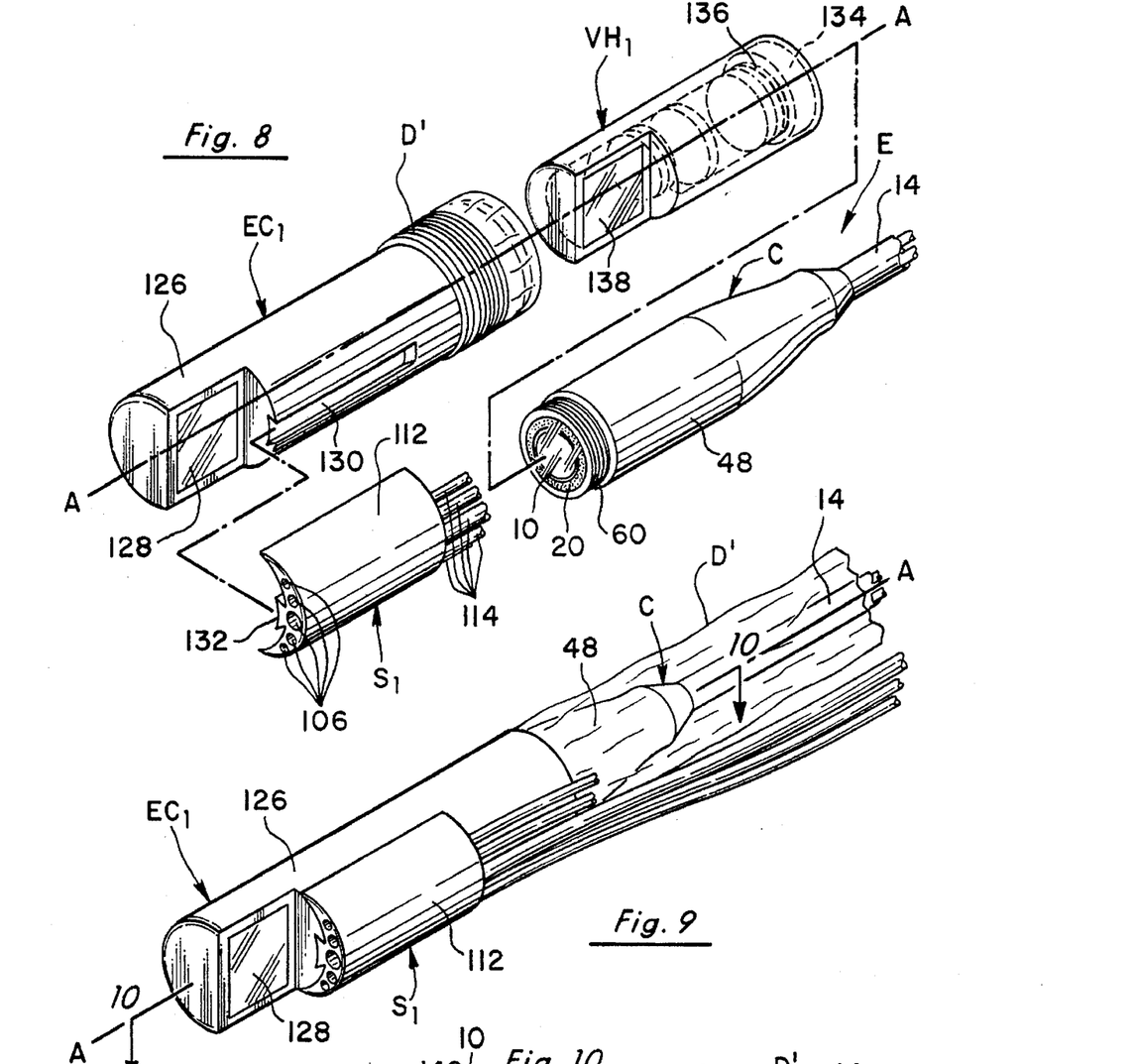
FIG. 8 is a fragmentary exploded perspective view of a third embodiment of this invention wherein a viewing head enables side viewing and the separable channel section attaches to the end cap resulting in a substantially cylindrical cross-section.
FIG. 9 is a fragmentary perspective view of the invention in FIG. 8.
Figure 10:
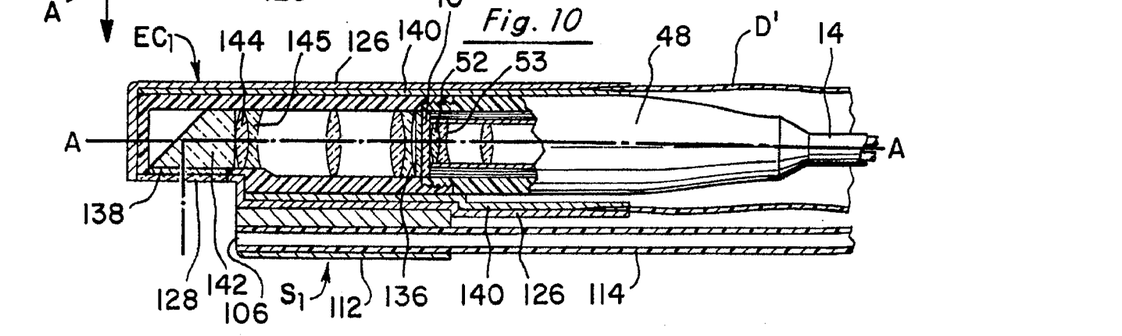
FIG. 10 is a partial longitudinal section taken along line 10—10 of FIG. 9 illustrating the interior relationship of the elements when assembled for use.

FIG. 8 illustrates yet another embodiment of this invention wherein the viewing head $VH_1$ allows side viewing of the operative site. Accordingly, end cap $EC_1$ also includes side viewing window 128 to match viewing head window 138 of viewing head $VH_1$ so that side viewing may be achieved. Additionally, separable channel section $S_1$ may be modified such that it has a crescent shape exterior 112, resulting in a substantially oval or oblong cross-sectional shape when the end cap $EC_1$ is attached to the separable channel section $S_1$. As with the previous embodiments, the separable channel section $S_1$ may include a plurality of channels 106 to transmit fluid, gas or to provide a channel for receiving an operative instrument. Communicating with the plurality of channels 106 are corresponding plurality of tubes 114 which extend proximally away from the separable channel section $S_1$ and which communicate with the respective sources of fluid, gas or operative instruments. In this embodiment, the drape D' is accordion folded as opposed to roll folded as illustrated in the previous embodiments. Depending upon how the end cap is packaged prior to use, either a roll fold or accordion fold may be advantageous. The end cap $EC_1$ includes an outer end cap wall 126 and, as previously mentioned, a viewing window 128 enabling side viewing of the operative site. A keyway 130 is formed along the outer end cap wall 126 and is engageable with a key 132 of the separable channel section $S_1$. Thus, in order to engage the separable channel section $S_1$ with the end cap $EC_1$ one simply may snap the elements together, or alternatively, key 132 may be slid along keyway 130. As with the previous embodiment, viewing head $VH_1$ may also include internal threads 134 to engage with external threads 60 of capsule C. As best seen in FIG. 10, viewing head $VH_1$ includes a proximal viewing head window 136, a side viewing window 138 and viewing head lenses 144 and 145 in order that the desired type of image may be transmitted to the CCD located within the capsule C. A prism 142 adjacent lenses 144 and 145 causes reflected light to be bent at a 90° angle so that side viewing can be achieved. As with the previous embodiments, the end cap $EC_1$ may be attached to the drape D' by capturing the end of the drape between outer end cap wall 126 and inner end cap wall 140.

Figures 11, 12:
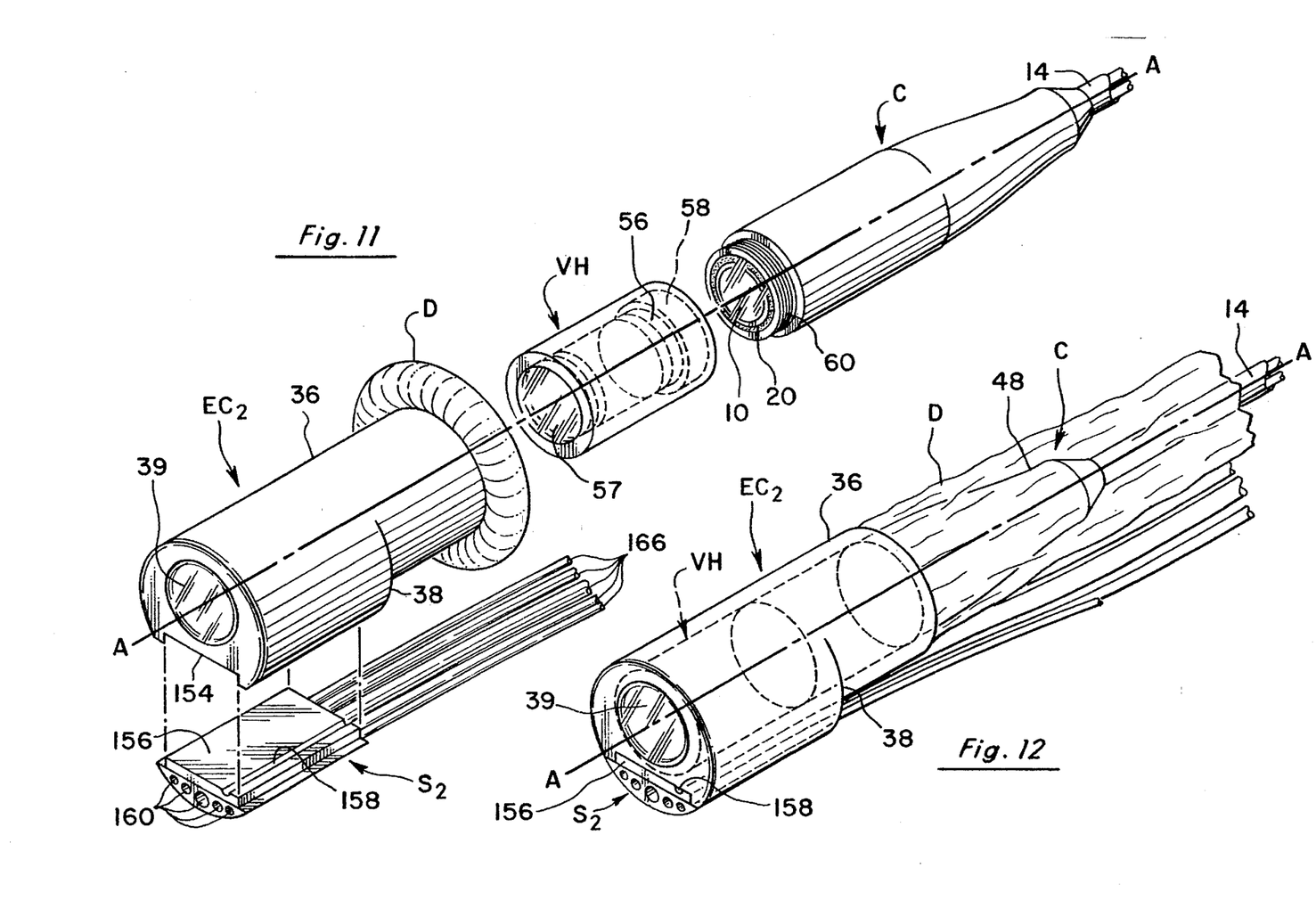
FIG. 11 is a fragmentary exploded perspective view of a fourth embodiment of this invention, with the drape rolled up, illustrating a separable channel section that includes a flat mating surface having a magnet for attachment to a ferrous surface on the end cap.
FIG. 12 is a fragmentary perspective view of the invention in FIG. 11 with the drape extended.

In yet another embodiment of the invention, as best seen in FIGS. 11 and 12, a separable channel section $S_2$ may be modified to include a magnet 156 which is engageable with a ferrous engaging surface 154 of end cap $EC_2$. The separable channel section $S_2$ of this embodiment may also include a guide wire channel 158 in the event a steerable endoscope is used. A plurality of channels 160 communicate with corresponding tubes 166 in order to allow transmission of fluid, gas or operative instruments to the operative site. In operation, the separable channel section $S_2$ is simply pressed against the ferris engaging surface 154 wherein the magnetic attraction between the members allows the separable channel section $S_2$ to be releasably held against the end cap $EC_2$.

Although the magnet 156 is shown as attached to the separable channel section $S_2$, it is well within the knowledge of those skilled in the art to place the magnet 156 on the end cap $EC_2$ in order to engage with a ferrous engaging surface 154 locatable on the separable channel section $S_2$.

Figures 13, 14, 15:
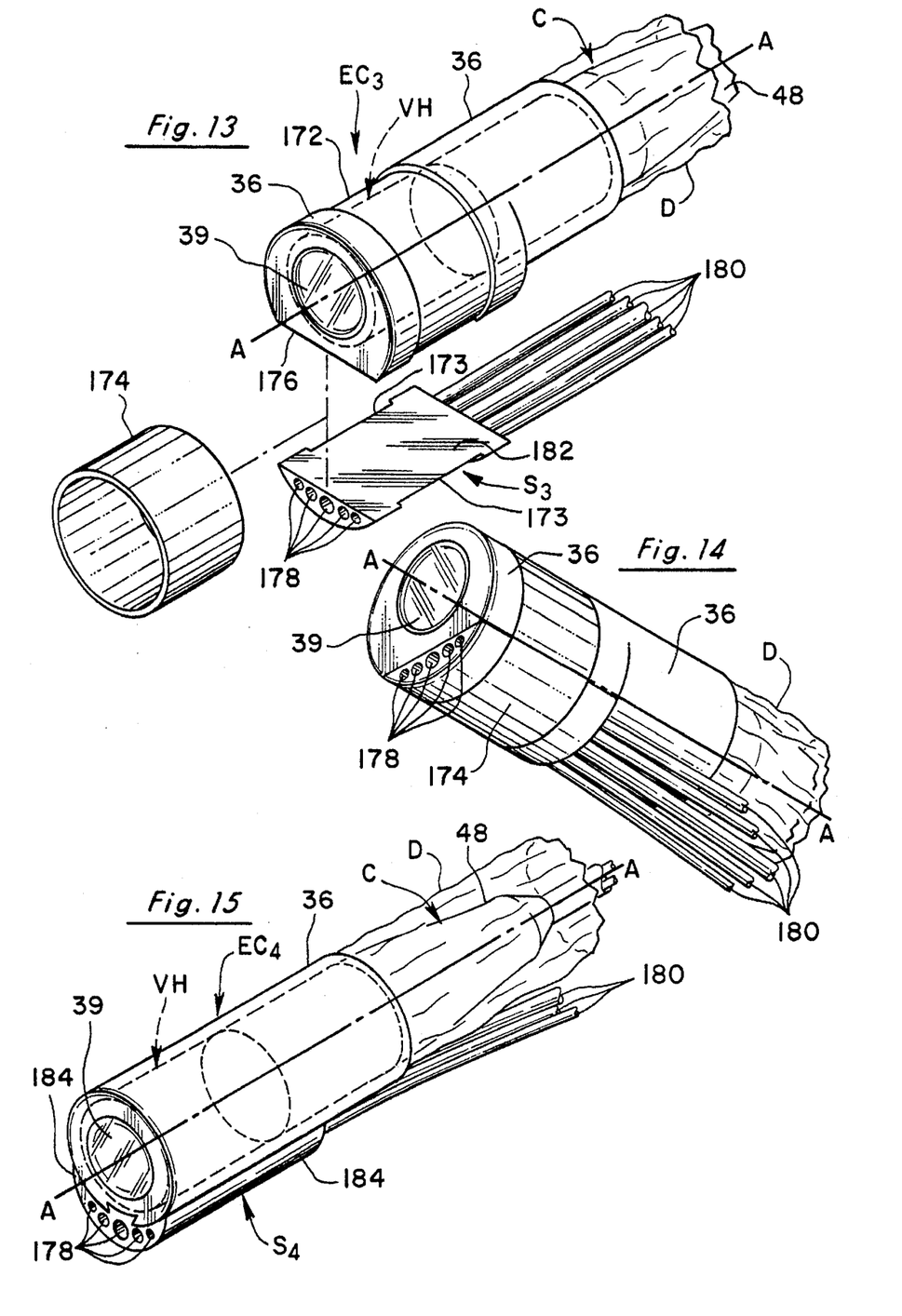
FIG. 13 is a fragmentary exploded perspective view of a fifth embodiment of this invention illustrating a separable channel section attachable to the end cap by a retaining band.
FIG. 14 is a fragmentary perspective view of the invention in FIG. 13.
FIG. 15 is a fragmentary perspective view of a sixth embodiment of this invention illustrating a separable channel section like that shown in FIG. 8 but wherein the endoscope is an end viewing device.

FIG. 13 is yet another embodiment of the disclosed invention wherein a separable channel section $S_3$ is attached to an end cap $EC_3$ by means of a retainer band 174 that fits in retainer slot 172. The retainer slot 172 extends circumferentially around the end cap $EC_3$ and corresponds with a retainer slot 173 formed in circumferential relationship around the separable channel section $S_3$. As with the other embodiments, a plurality of channels 178 are provided that communicate with plurality of tubes 180 for transmission of fluid, gas or an operative instrument to the operative site. As shown in FIG. 14, placing the retainer band 174 in retainer slots 172 and 173 results in attachment of the separable channel section $S_3$ to the end cap $EC_3$ such that a substantially circular or oval cross-section shape is achieved. Accordingly, the separable channel section $S_3$ includes a second flat mating surface 182 that engages with a first flat mating surface 176 of the end cap $EC_3$.

In yet another embodiment, as shown in FIG. 15, separable channel section $S_4$, which is similar to that shown in FIG. 8, may also be configured so that the endoscope is an end viewing device. Crescent shape exterior 184 and outer end cap wall 36 form a smooth and contiguous cross-sectional shape when the separable channel section $S_4$ is attached to the end cap $EC_4$.

From the foregoing, the advantages of this invention are readily apparent. An endoscope with a separable auxiliary assembly has been provided having a disposable sterile separable channel section and a disposable end cap with attached drape so that after use, the end cap, drape and separable channel section can be separated from the endoscope and thrown away. Since the endoscope is completely shielded from the operative or surgical site, it is ready for subsequent use in another operative procedure without the need for disinfecting or sterilization. The use of a viewing head attached to the distal end of the endoscope enable a surgeon to obtain a multitude of desired viewing possibilities. Because of the novel arrangement of the end cap and separable channel section, the endoscope when introduced into a body cavity maintains a small size which reduces trauma for the patient. With the use of guide wires from a steerable endoscope, the distal end of the endoscope is steerable and may be precisely positioned during an operative procedure.

This invention has been described in detail with reference to particular embodiments thereof, but it will be understood that various other modifications can be effected within the spirit and scope of this invention.

I claim:

1. An apparatus for viewing a surgical operative site and conducting operative procedures in a sterile environment such as that of an operating room, said apparatus comprising:

an endoscope including a distal capsule portion, and means for transmitting an image of the operative site disposed within said capsule;

an end cap having an inner and outer surface, proximal and distal ends, and a first mating surface formed along at least a portion of said end cap outer surface, said capsule being insertable within space defined by said inner surface of said end cap; and a separable disposable channel section having at least one longitudinal opening for transmitting fluids or gas or for receiving an operative instrument, and further including a second mating surface formed on said separable channel section for releasable attachment of said second mating surface to said first mating surface of said end cap.

2. Apparatus, as claimed in claim 1, further including:
a sterile drape attachable to said proximal end of said end cap and extendable over said endoscope when said capsule is inserted within said end cap for shielding said endoscope from the sterile environment.

3. Apparatus, as claimed in claim 1, wherein said end cap further includes:
an optically clear window attached to said distal end of said end cap providing a sterile barrier between said capsule and the sterile environment.

4. Apparatus, as claimed in claim 1, wherein:
said endoscope is an end viewing device.

5. Apparatus, as claimed in claim 1, further including:
a viewing head having first and second ends, said first end of said viewing head releasably attachable to said capsule and said viewing head being insertable with said capsule into said end cap for providing a desired viewing field or an enhanced image of the surgical operative site.

6. Apparatus, as claimed in claim 5, wherein:
said first end of said viewing head includes threads formed along an interior edge therealong; and
said capsule includes exterior threads for releasably engaging said viewing head interior threads.

7. Apparatus, as claimed in claim 1, wherein said end cap further includes:
an optically clear window attached to said outer surface of said end cap providing a sterile barrier between said capsule and the sterile environment; and
a prism positionable adjacent said window and inside said end cap so that said endoscope is a side-viewing device.

8. Apparatus, as claimed in claim 1, wherein said separable channel section further includes:
a channel formed along said second mating surface for receiving a guide wire whereby said distal end of said end cap is steerable for manipulation of said endoscope to a desired location.

9. Apparatus, as claimed in claim 1, further including:
a flexible tube having a distal end correspondingly connected to said at least one longitudinal opening of said separable section for supplying fluid or gas or for receiving the operative instrument from a remote location, said flexible tube positionable adjacent to and exteriorly of said endoscope.

10. An apparatus, as claimed in claim 1, wherein:
one of said first and second mating surfaces comprises a longitudinal flat and a keyway forming a recessed portion integral with said flat; and
the other of said first and second mating surfaces includes a longitudinal key which is engageable with said keyway.

11. Apparatus, as claimed in claim 1, wherein:
said separable disposable channel section and said end cap when attached form a substantially circular cross section.

12. Apparatus, as claimed in claim 1, wherein:
said separable disposable channel section and said end cap when attached form a substantially oval shaped cross section.

13. Apparatus as claimed in claim 1, wherein:
one of said first and second mating surfaces includes a ferrous material; and
the other of said first and second mating surfaces includes a magnetic strip for releasable magnetic attachment of said separable section to said end cap.

14. Apparatus, as claimed in claim 1, further including:
a retaining band positionable over said end cap and said separable disposable channel section for releasably attaching said separable disposable channel section to said end cap.

15. A method of providing endoscopic imagery of a sterile surgical operative site during an operative procedure wherein operative fluids, gases or instruments may be applied to the site from a remote location, said method comprising the steps of:
providing a sterile end cap including a first outer surface;
inserting the distal end of an endoscope into the sterile end cap;
attaching a separable channel section including a second outer surface to the first outer surface of the end cap for providing operative fluids, gases or instruments to the operative site; and
viewing the surgical operative site via the endoscope.

16. A method, as claimed in claim 15, further including the steps of:
providing a sterile drape attachable to the sterile end cap; and
extending the drape over the endoscope and trailing endoscope cables to shield the endoscope and cables from the surgical operative site.

17. A method, as claimed in claim 15, further including the steps of:
introducing the desired fluids, gases or operative instruments through the separable channel section; and
conducting the necessary operative procedure via the separable channel section.

18. A method, as claimed in claim 15, further including the steps of:
attaching a detachable viewing head to the endoscope before inserting the endoscope into the sterile end cap, the viewing head providing a desired viewing field or an enhanced image of the operative site.

19. A method, as claimed in claim 15, further including the step of:
detaching the separable channel section from the end cap; and
attaching another separable channel section to the end cap during the same operative procedure without having to remove the endoscope from the sterile end cap.

20. A device for viewing a surgical operative site and conducting operative procedures in a sterile environment such as that of an operating room, said device comprising:
an endoscope including a distal capsule portion, and means for transmitting an image of the operative site to a viewing device, said transmitting means being disposed within said capsule;
an end cap having an inner and outer surface, proximal and distal ends, and a first mating surface formed along at least a portion of said end cap outer surface, said capsule being insertable within said end cap; and
a separable disposable channel section having at least one longitudinal opening therethrough, and further including a second mating surface formed on said separable channel section for releasable attachment of said second mating surface to said first mating surface of said end cap, said separable section and said end cap when attached by said first and second mating surfaces form a predetermined cross section.

21. Apparatus, as claimed in claim 20, further including:

a sterile drape attachable to said end cap and extendable over said endoscope for shielding said endoscope from the sterile environment.

22. Apparatus, as claimed in claim 20, wherein:

said predetermined cross section is substantially circular shaped.

23. Apparatus, as claimed in claim 20, wherein:

said predetermined cross section is substantially oval shaped.

24. Apparatus, as claimed in claim 20, wherein:

said predetermined cross section is substantially oblong shaped.

25. A separable auxiliary assembly for releasable attachment to an endoscope, the separable auxiliary assembly shielding the endoscope and its trailing cables from a sterile environment such as that of an operating room, said separable auxiliary assembly enabling fluid, gas, or surgical instruments to be applied to an operative site, said separable auxiliary assembly comprising:

an end cap having an inner and outer surface, proximal and distal ends, and a first mating surface formed along at least a portion of said end cap outer surface; and a separable disposable channel section having at least one longitudinal opening for transmitting fluids, gas, or for receiving an operative instrument, and further including a second mating surface formed on said separable channel section for releasable attachment of said second mating surface to said first mating surface of said end cap, said separable section and said end cap when attached by said first and second mating surfaces form a predetermined cross section.

26. Apparatus, as claimed in claim 25, further including:

a sterile drape attached to said end cap and extendable over the endoscope and its trailing cables for shielding the endoscope and its trailing cables from the sterile environment.

27. Apparatus, as claimed in claim 25, wherein:

said predetermined cross section is substantially circular shaped.

28. Apparatus, as claimed in claim 25, wherein:

said predetermined cross section is substantially oval shaped.

29. Apparatus, as claimed in claim 25, wherein:

said predetermined cross section is substantially oblong shaped.

30. An apparatus for viewing a surgical operative site and conducting operative procedures in a sterile environment such as that of an operating room, said apparatus comprising:

an endoscope including a distal capsule portion;

an end cap having an inner and outer surface, proximal and distal ends, and a first substantially planar mating surface formed along at least a portion of said end cap outer surface, said distal capsule portion being insertable within spaced defined by said inner surface of said end cap; and a separable channel section including an outer surface, at least one opening for transmitting fluids or gas or for receiving an operative instrument, and further including a second substantially planar mating surface formed on at least a portion of said outer surface of said separable channel section for releasable attachment of said second mating surface to said first mating surface of said end cap.

31. An apparatus, as claimed in claim 30, further including:

a sterile drape attachable to said proximal end of said end cap and extendable over said endoscope when said distal capsule portion is inserted within said end cap.

32. An apparatus, as claimed in claim 30, wherein said end cap further includes:

an optically clear window attached to said distal end of said end cap.

33. An apparatus, as claimed in claim 30, further including:

a viewing head having first and second ends, said first end of said viewing head releasably attached to said distal capsule portion and said viewing head being insertable with said distal capsule portion into said end cap for providing a desired viewing field or an enhanced image of the surgical operative site.

34. An apparatus, as claimed in claim 30, wherein said end cap further includes:

an optically clear window attached to said outer surface of said end cap; and a prism positionable adjacent to said window and inside said end cap so that said endoscope is a side viewing device.

35. An apparatus, as claimed in claim 30, wherein said separable channel section further includes:

a channel formed along said second mating surface for receiving a guide wire whereby said distal end of said end cap is steerable for manipulation of said endoscope to a desired location.

36. An apparatus, as claimed in claim 30, further including:

a flexible tube having a distal end connected to said at least one opening of said separable channel section, said flexible tube positionable adjacent to and exteriorly of said endoscope.

37. An apparatus, as claimed in claim 30, wherein:

one of said first and second mating surfaces includes a longitudinal flat and a key way forming a recessed portion integral with said longitudinal flat; and the other of said first and second mating surfaces includes a longitudinal key which is engageable with said key way.

38. An apparatus, as claimed in claim 30, wherein:

said separable channel section and said end cap when attached form a substantially circular shaped cross-section.

39. An apparatus, as claimed in claim 30, wherein:

said separable channel section and said end cap when attached form a substantially oval shaped cross-section.

40. An apparatus, as claimed in claim 30, wherein:

one of said first and second mating surfaces includes a ferrous metal; and the other of said first and second mating surfaces includes a magnetic strip for releasable magnetic attachment of said separable channel section to said end cap.

41. An apparatus, as claimed in claim 30, further including:

a retaining band positionable over said end cap and said separable channel section for releasably attaching said separable channel section to said end cap.

42. A method of providing endoscopic imagery of a surgical operative site during an operative procedure, wherein operative fluids, gases or instruments may be applied to the site from a remote location, said method comprising the steps of:

provide a sterile end cap including a first substantially planar mating surface;

inserting a distal end of an endoscope into the sterile end cap;

attaching a separable channel section including a second substantially planar mating surface to the first substantially planar mating surface of the end cap for providing operative fluids, gases or instruments to the operative site; and viewing the surgical operative site via the endoscope.

43. A method, as claimed in claim 42 further including the step of:

detaching the separable channel section from the end cap without removing the distal end of the endoscope from within the sterile end cap; and attaching another separable channel section to the end cap without removing the endoscope from within the sterile end cap.

44. A separable auxiliary assembly for releasable attachment to an endoscope, the separable auxiliary assembly shielding the endoscope from a sterile environment such as that of an operating room, said separable auxiliary assembly enabling fluid, gas, or surgical instruments to be applied to an operative site, said separable auxiliary assembly comprising:

an end cap having a first substantially planar mating surface formed on at least a portion of said end cap; and a separable channel section having an outer surface, at least one opening for transmitting fluids or gas or for receiving an operative instrument, and further including a second substantially planar mating surface formed on at least a portion of said outer surface of said separable channel section for releasable attachment of said second mating surface to said first mating surface of said end cap.

45. A separable auxiliary assembly for releasable attachment to an endoscope, the separable auxiliary assembly shielding the endoscope from a sterile environment such as that of an operating room, said separable auxiliary assembly enabling fluid, gas, or surgical instruments to be applied to an operative site, said separable auxiliary assembly comprising:

an end cap having a concave mating surface formed on at least a portion of said end cap; and a separable channel section having at least one opening for transmitting fluids or gas or for receiving an operating instrument, and further including a convex mating surface formed on said separable channel section for releasable attachment of said convex mating surface to said concave mating surface of said end cap.

46. An apparatus for viewing a surgical operative site and conducting operative procedures, said apparatus comprising:

an endoscope including a distal capsule portion;

an end cap having an inner and outer surface, proximal and distal ends and a concave mating surface formed along at least a portion of said end cap outer surface, said distal capsule portion being insertable within space defined by said inner surface of said end cap; and a separable channel section having at least one opening for transmitting fluids or gas or for receiving an operative instrument, and further including a convex mating surface formed on said separable channel section for releasable attachment of said convex mating surface to said concave mating surface of said end cap.

47. A method of providing endoscopic imagery of a surgical operative site during an operative procedure wherein operative fluids, gases or instruments may be applied to the site from a remote location, said method comprising the steps of:

providing a sterile end cap including an external concave mating surface;

inserting a distal end of an endoscope into the sterile end cap;

attaching a separable channel section including an external convex mating surface to the external concave mating surface of the end cap for providing operative fluids, gases or instruments to the operative site; and viewing the surgical operative site via the endoscope.

48. A method, as claimed in claim 47, further including the step of:

detaching the separable channel section from the end cap without removing the endoscope from within the sterile end cap; and attaching another separable channel section to the end cap without removing the endoscope from within the sterile end cap.

* * * * *